United States Patent [19]

Varma

[11] Patent Number: 5,032,392

[45] Date of Patent: Jul. 16, 1991

[54] AQUEOUS OPHTHALMIC SOLUTIONS FOR THE TREATMENT OF DRYNESS AND/OR IRRITATION OF HUMAN OR ANIMAL EYES

[75] Inventor: Shambhu D. Varma, Ellicott City, Md.

[73] Assignee: Vision Pharmaceuticals, Bel Air, Md.

[21] Appl. No.: 903,597

[22] Filed: Sep. 4, 1986

[51] Int. Cl.$^5$ .................... A61K 31/74; A61K 31/70; A61K 31/07

[52] U.S. Cl. ........................................ 424/78; 514/39; 514/725

[58] Field of Search ..................... 424/78; 514/39, 912

[56] References Cited

U.S. PATENT DOCUMENTS

| | | | |
|---|---|---|---|
| 3,384,545 | 5/1968 | Aiello et al. | 424/81 |
| 4,219,545 | 8/1980 | Collins et al. | 514/39 |
| 4,409,205 | 10/1983 | Shively | 424/78 |
| 4,421,748 | 12/1983 | Trager et al. | 514/912 |

FOREIGN PATENT DOCUMENTS

1431841  4/1976  United Kingdom .

OTHER PUBLICATIONS

Tseng et al.-Ophthalmology 92,717-727 (1985) "Topical Retinoid Treatment for Various Dryeye Disorders".
Tseng et al.-"Topical A Treatment for DryEye Disorders" 10-2-84, Science Writers Seminar in Ophthalmology.
Edelhauser et al.-Arch Ophthalmol. 93,648-655 & 657, "Intraocular Irrigating Solutions".
Chem. Abst. 96:223,307 p. (1982)-Urquhart.

Primary Examiner—Stanley J. Friedman
Assistant Examiner—Zohreh A. Fay
Attorney, Agent, or Firm—Venable, Baetjer, Howard & Civiletti

[57] ABSTRACT

An aqueous ophthalmic preparation is described for the treatment of dry and/or irritated eyes. The preparation is comprised of retinol and/or derivatives or precursors thereof, solubilized in water. Certain non-ionic surfactants and propylmethylcellulose are disclosed as solubilizing agents, with propylmethylcellulose also acting as a mucin-like constituent. The vitamin-containing preparation also contains (1) free radical scavenging compounds and (2) compounds capable, in solution, of chelating multivalent metal cations present in human and/or animal external eye tissue or tear film. The preferred free radical scavenger is mannitol. The preferred chelating agent is EDTA, present in minimal quantities for chelating certain catalytically active metallic ions present at or near the surface of the eye. Also described are tonicity adjusting compositions and an ophthalmic solution buffering system comprising citric acid and citrates.

62 Claims, No Drawings

AQUEOUS OPHTHALMIC SOLUTIONS FOR THE TREATMENT OF DRYNESS AND/OR IRRITATION OF HUMAN OR ANIMAL EYES

BACKGROUND OF THE INVENTION

Field of the Invention

The present invention relates to an aqueous ophthalmic preparation for humans as well as animals. The opthalmic preparation comprises Vitamin A and other free radical scavengers. Ophthalmic preparations comprising citric acid and citrates are also described.

DESCRIPTION OF THE PRIOR ART

The Problem Addressed

The anterior portion of the eye remains exposed to light and contents of the air, including pollutants, continuously during the day, as well as in the evening before sleeping hours. This constant exposure can promote evaporation and consequent dryness of the external surface of the cornea and the conjunctiva causing discomfort, irritation and consequent impairment of vision. Generally the fluid lost by evaporation and drainage through the lacrimal duct is replaced. This is achieved through a continuous production of the tear film consisting of an inner mucin layer, a middle aqueous layer and an outer lipid layer. This trilayer tear film is produced by the concerted action of (1) Goblet cells producing the mucin, (2) the primary and accessory lacrimal glands producing the aqueous layer, and (3) Meibomian and the other glands producing the lipid layer. The ability of the various glandular structures situated in the conjunctiva and the lid propria to produce the required components of the tear film may be impaired as a sequel to a disease of the conjunctiva and the eyelids, or as a result of age-related dysfunction of the secretory glands and/or cells.

The Prior Art Addressing the Problem

Application of ophthalmic preparations such as demulcents and artificial tears can sometimes help to alleviate the resulting discomforting symptoms of excessive dryness and aid in the natural healing of the injured conjunctival and corneal tissue resulting from either dryness, abrasion or contact lens related complications.

Vitamin A normally derived from foods is known to be an essential element that must be present for maintenance and function of epithelial cells and adaptation to light and night vision. Diets deficient in Vitamin A result in xerosis of the eye and kerato-conjunctivitis. Cases of severe and prolonged Vitamin A deficiencies often lead to blindness. The acid form of Vitamin A (retinoic acid) has been used to treat excessive dryness in petroleum based, non-aqueous, ointments; also, Vitamin A palmitate has been administered orally to treat dryness of the eye (xerosis).

SUMMARY OF THE INVENTION

While the symptoms of dryness can be alleviated by many physiologically compatible topical drop treatments, a more ideal treatment should involve instillation of physiological substances to maintain the secretory activity of the eye's tear producing glandular structure; Goblet cells, the lacrimal glands and the lipid producing glands. Heretofor Vitamin A and/or its derivatives have not been administered in drop treatments in an aqueous solution either alone or in combination with water-soluble ingredients that have (1) an additive effect in the maintenance and protection of the eye's tear producing glandular structure and/or (2) an additive effect in maintaining and protecting other external eye tissues.

In accordance with the present invention, Vitamin A in combination with other ingredients in an aqueous solution is topically applied to the epithelial cells of the cornea and conjunctiva. Such application serves to maintain secretory activity and also to regenerate epithelial cells in places where they are not functioning optimally because they have been damaged.

Also, in accordance with the present invention, citrate ions are used in aqueous ophthalmic solutions where they function by inhibiting the attack of the relevant sites by polymorphonuclear leucocytes. These leucocytes liberate large quantities of free radicals of oxygen which are oxidative in nature. Also, the citrate acts as a normal cell nutrient providing bioenergetic advantage. The citrate ions also may be used as buffer constituents as well.

One object of the invention is to provide an ophthalmic preparation to alleviate discomforting symptoms of excessive dryness and aid in the natural healing of the injured conjunctival and corneal tissue resulting from dryness, abrasion or complications from wearing contact lenses.

Another object of the present invention is to provide Vitamin A and one or more free radical scavengers in the form of an aqueous preparation.

A further object of the present invention is to provide an aqueous Vitamin A solution wherein a water-soluble antioxidant mannitol is present in an amount effective to reduce hydroxyl radicals present in (1) the outer surface of the eye (the external eye tissues), that is, the lids, conjunctiva, inclusive of glands, the cornea and sclera; and, (2) the tear film.

Another aspect of the invention is the use of a buffer comprising citrate ions which serves a multifunctional purpose in aqueous ophthalmic compositions based on its affect as an antioxidant and cell nutrient.

Yet another object of the present invention is to provide an ophthalmic aqueous solution of specific composition such that Vitamin A is maintained in solution at appropriate concentrations along with (1) one or more free radical scavengers, (2) an alkali salt, sucrose or other tonicity maintaining constituents, and (3) a buffer. The buffer maintains the pH of the solution within the range suitable for ophthalmic preparations. The tonicity affecting constituent(s) are used where an isotonic solution is desired for maintenance of osmotic balance similar to that of the natural tear film.

In the preferred embodiment of the invention, retinol as such is delivered topically to the eye in an aqueous solution. This insures the availability of Vitamin A in its active form without need for any transformation of Vitamin A derivatives or precursors to active retinol.

In yet a further aspect of the present invention, the ophthalmic preparation for the treatment of dry eyes comprises an aqueous solution containing a physiologically acceptable free radical scavenger; and a physiologically acceptable metal chelating agent for multivalent metal cations present in human and animal external eye tissue or tear film. The free radical scavenger mannitol and ethylenediamine tetraacetate as chelating agent are preferred.

DETAILED DESCRIPTION OF THE INVENTION

The present invention allows for delivery of Vitamin A in the form of retinol, other Vitamin A derivatives inclusive of retinoic acid and the fatty acid ester derivatives and also Vitamin A precursors, e.g., carotenes in an aqueous solution. The solution further comprises one or more antioxidants (free radical scavengers) that increase the stability of the Vitamin A in the solution and that enhance the effectiveness of the solution to defend against the damaging effects of free radicals of oxygen. The free radicals involved are superoxide, hydroxyl radicals, peroxyl radicals and the like. These radicals are generated during most oxidative processes that take place in the tissue or externally in the tear film. Hydroxyl radicals are derivatives of a complex series of chemical reactions that occur on the eye surface. The hydroxyl radical is a potent oxidant and is believed to be an important agent of cellular injury.

The free radical scavengers in the ophthalmic solution scavenge oxygen and hydroxyl radicals present in the external eye tissue and/or the tear film.

The presence of free radical scavengers (oxidants) also serves to minimize oxidation of the solubilized retinol while in the solution. The prevention of retinol from oxidation is crucial to its biological activity.

Free radical scavenger is defined as a substance which (1) removes the lone electron from a free radical; (2) which adds an electron to the free radical to convert same into a less reactive ion; or, (3) which dismutates a free radical to a non-radical product or products.

In one preferred embodiment of the invention, the ophthalmic solution contains mannitol as a free radical scavenger. Mannitol is a very effective free radical scavenger of the hydroxyl radical when used in the ophthalmic solutions of the present invention. Mannitol is preferably present in an amount of from about 0.9 mg/ml. to about 3.6 mg/ml.

In another preferred embodiment of the invention the solution contains a biologically compatible chelating agent, a non-toxic chelating agent for metallic ions that are present in the external eye tissue and in the tear film of the eye. Specifically contemplated as useful are chelating agents for trace metals which include iron, manganese, copper and other multivalent metals present in body fluids such as tear secretion, which may also be introduced in the eye externally from atmospheric pollutants. These metals catalyze generation of free radicals capable of inducing oxidation damage to the tissue. Chelation of these metals is believed to prevent free radical formation catalyzed by the chelated metals in the unchelated form. For this purpose ethylenediamine tetraacetate, EDTA, is the most preferred agent. The EDTA acts as an antioxidant by preventing/limiting the generation of metal catalyzed free radicals of oxygen that occurs when the metals are exposed to an oxygen environment.

EDTA suitably is present in the solution in an amount of from about 0.05 mg/ml. to about 0.1 mg/ml.

Other acceptable chelating agents such as amino acids, like glutamic and aspartic acids and borates may be used, although not necessarily with equivalent results.

In addition, the present invention involves the use of buffering and/or tonicity imparting agents that provide an isotonic solution of a pH approximating that of tears, whereby the solution may be applied with no discomfort and with maintenance of an osmotic balance similar to that of the natural tear film.

The tonicity of the solution, although it may be varied to provide hypotonic or hypertonic ophthalmic solutions for specific ophthalmic applications, most preferably approximates the isotonicity of the tear. Preferred tonicity, per kg. of the solution, is $300\pm25$ mOsm per kg. of water. The most preferred tonicity is $300\pm10$ mOsm per kg. of water. The most highly preferred tonicity substantially matches the tonicity of the tear.

In the opthalmic solution of the present invention, desired tonicity is suitably obtained utilizing a biologically compatible (alternatively referred to as physiologically acceptable/non-toxic) alkali salt such as sodium or potassium chloride.

Alkali salt can be replaced by other non-toxic tonicity compensating substances such as sucrose and sorbitol. The preferred alkali salt in this formulation is sodium chloride, which suitably is present in the solution in amounts of from about 5 to about 9 mg/ml. Equivalent amounts of sucrose, which may also be used, are from about 50 to about 100 mg/ml. The attraction of replacing alkali salts by sucrose and like polyhydroxy non-toxic food constituents (sugar and other carbohydrates) lies in the ability of the latter to prevent oxidation by hydroxyl radicals that may be generated in the external eye and/or the tear film as the result of ambient or photocatalyzed oxygen utilization.

The pH of the solution is adjusted within the pH allowable for ophthalmic preparations generally. The normal pH of tears in humans is about 7.5 for the open eye and about 7.2 for the closed eye. This range, therefore, defines the optimal pH level of the ophthalmic solution of the invention. The most preferred pH would proximate that of the tear film and be within the range of from about 7.1 to about 7.6. Preferably the solution of the present invention has a pH within the range of from about 6.6 to about 7.8. Outside such range, solutions have a tendency to cause irritation.

The selected range of pH can be achieved and maintained in the solution utilizing suitable biologically compatible (physiologically acceptable) buffering compositions.

The most highly preferred means of maintaining the required pH is by the use of a combination of citric acid and Na or K citrate. Phosphate salts, such as monosodium dihydrogenphosphate, disodium monohydrogenphosphate, monopotassium dihydrogenphosphate and/or dipotassium monohydrogen phosphate, may also be used as buffering agents. The preferred concentration of citric acid is from about 0.03 mg/ml. to about 0.06 mg/ml.

Other metabolic acids, such as lactic, maleic and succinic acids may be used in place of citric acid, but citric acid is by far the metabolic acid of choice, because the citric acid and alkali citrate system, for reasons noted below, serves multiple functions when incorporated in ophthalmic solutions.

Sodium citrate preferably is used at concentrations of from about 5 mg/ml. to about 10 mg/ml. The combination of citric acid and citrate serves the dual function in the aqueous solution of maintaining the required pH of the solution and providing nutritional support to the tissue. It also inhibits the invasion of damaged tissue by polymorph nuclear leucocytes. These leucocytes liberate oxygen radicals that damage tissue. In addition, citric acid is a component involved in tissue metabolism that oxidizes certain carbohydrates to $CO_2$ with concomitant liberation of energy. This process also produces other important cellular metabolites. The presence of additional citric acid is believed, therefore, to support the tissue metabolically. Citrate ions also function to maintain certain ions such as calcium and iron ions in chelated form, therefore, preventing deleterious metal catalyzed oxidation reactions. Accordingly, in one preferred embodiment of the invention, the solution comprises citric acid and sodium and/or potassium citrate with the citric acid present in an amount of from about 0.03 mg/ml. to about 0.06 mg/ml. and the citrate being present in an amount of from about 5 mg/ml. to about 10 mg/ml.

It is therefore, an important aspect of the present invention to use, in aqueous ophthalmic solutions, a combination of (1) citric acid and (2) sodium citrate, potassium citrate or admixtures of sodium citrate and potassium citrate to achieve the multiple result above-iterated.

A biologically compatible surfactant, suitably a water soluble surface acting agent possessing emulsifying and wetting properties, preferably a non-toxic surface active agent such as polyoxyalkylene derivatives of hexitol anhydride in the minimal amount necessary to dissolve and maintain retinol in solution in the aqueous carrying medium. Although higher levels of surfactant may be tolerated, it is preferred to use this component of the solution in the minimal amount required to achieve dissolution of retinol. Among the preferred surfactants are: Tween ®-80, Tween ®-60 and Tween ®-40 manufactured by I.C.I. United States, Wilmington, Del., all polyoxyalkyne sorbitan derivatives. These surfactants are preferred because it is believed they serve the dual purpose of (1) achieving, by virtue of their solubilizing and emulsifying activity, a pharmaceutically effective Vitamin A concentration in the aqueous solution and (2) functioning, to some degree, as free radical scavengers. The preferred surfactants are preferably present in an amount less than about 0.1% by weight based on the water present and most preferably in an amount of from about 0.05 mg/ml. to about 0.1 mg/ml. At levels above about 0.85% by weight, based on water, the Tween ® brand non-ionic surfactants increase oiliness and when the solution is placed on the eye may cause temporary blurred vision. Therefore, although the presence of such levels of surfactants may be tolerated without resultant tissue damage or other adverse physiological consequences, the potential for undesirable consequences (blurring) indicates surfactant usage in minimum quantities required for dissolving the retinol.

Optionally propylmethylcellulose or other similar cellulose derivatives can also be incorporated into the ophthalmic solution. These constituents aid in the dissolution of the retinol and function as wetting agents simulating the effect of mucin, a normal constituent of tears. Preferably propylmethylcellulose is present in an amount of from about 0.5 mg/ml. to about 1.5 mg/ml.

The ability of propylmethylcellulose and other similar cellulose derivatives to solubilize retinol allows ophthalmic solutions of retinol to be formulated where the surfactant component used for dissolution of the retinol to be replaced in whole or in part, depending on the solution requirements.

Thus, in yet another aspect, the present invention involves the use of propylmethylcellulose and/or equivalent cellulose derivatives in aqueous ophthalmic solutions containing water-insoluble compounds selected from the group consisting of retinol, retinol derivatives (retinoic acid inclusive) or retinol precursors which are insoluble in water.

EXAMPLES

Four examples of retinol-containing solutions of the present invention, illustrating the composition and the method of making such solutions, are noted below.

EXAMPLE I

The starting materials for preparation of the solution were as follows:

| | |
|---|---|
| Sodium chloride | 6.55 g |
| Trisodium citrate, monohydrate | 7.35 g |
| Citric acid | 0.035 g |
| EDTA Na$_2$ | 0.050 g |
| Mannitol | 1.8 g |
| H$_2$O | 1 L |
| Retinol | 120 mg |
| Tween ®-80 | 500 mg |

The retinol-containing solution was prepared by adding sodium chloride, trisodium citrate, citric acid monohydrate, EDTA Na$_2$ and mannitol in the amounts specified above to one liter of water. The foregoing constituents were dissolved and autoclaved at a pressure of 15 lbs. and a temperature of 120° C. and chilled to 4° C. 120 mg of retinol were dissolved in 500 mg of Tween ®-80 by gentle warming at about 50° C. and shaking by hand and transferred quantitatively to 1 liter of the above mixture under constant magnetic stirring under chilling conditions. The mixture was stirred overnight. A clear solution was obtained. This solution was stored in a refrigerator at about 4° C. till used. The final concentration of retinol was determined by high pressure liquid chromatography on C-18 column, using a 95% methanol 5% H$_2$O mixture as the eluting solvent and monitoring the effluent spectrometrically at 290 and 328 nanometers. The concentration of retinol remained stable for at least six weeks. The solution was stored in a dark bottle at 4° C.

EXAMPLE II

The starting materials for preparation of the solution were as follows:

| | |
|---|---|
| Sodium chloride | 6.55 g |
| Trisodium citrate monohydrate | 7.35 g |
| Citric acid | 0.035 g |
| EDTA Na$_2$ | 0.050 g |
| Mannitol | 1.800 g |
| Propylmethylcellulose | 1.00 g |
| H$_2$O | 1 L |
| Retinol | 120 mg |
| Tween ®-80 | 500 mg |

The solution was prepared by adding sodium chloride, trisodium citrate, citric acid monohydrate, EDTA Na$_2$, mannitol and propylmethylcellulose in the amounts specified above to one liter of water. The foregoing constituents were dissolved and autoclaved at a pressure of 15 lbs. and a temperature of 120° C. and chilled to 4° C. 120 mg of retinol were dissolved in 500 mg of Tween ®-80 by gentle warming at about 50° C. and shaking by hand and transferred quantitatively to 1 liter of the above mixture under constant magnetic stirring. The mixture was stirred overnight in cold room (4° C.). A clear solution was obtained. This solution was stored in a refrigerator at about 4° C. till used. The final concentration of retinol was determined by high pressure liquid chromatography on C-18 column, using a 95% methanol 5% H$_2$O mixture as the eluting solvent and monitoring the effluent spectrometrically at 290 and 328 nanometers. The concentration of retinol remained stable for at least six weeks. The solution was stored in a dark bottle at 4° C.

EXAMPLE III

The starting materials for preparation of the solution were as follows:

| | |
|---|---|
| Sucrose | 76 g |
| Trisodium citrate monohydrate | 7.35 g |
| Citric acid | 0.035 g |
| EDTA Na$_2$ | 0.050 g |
| Mannitol | 1.8 g |
| H$_2$O | 1 L |
| Retinol | 120 mg |
| Tween ®-80 | 500 mg |

The retinol-containing solution is prepared by adding sodium chloride, trisodium citrate, citric acid monohydrate, EDTA Na$_2$ and mannitol in the amounts specified above to one liter of water. The foregoing constituents are dissolved and autoclaved at a pressure of 15 lbs. and a temperature of 120° C. and chilled to 4° C. 120 mg of retinol are dissolved in 500 mg of Tween ®-80 by gentle warming at about 50° C. and shaking by hand and transferred quantitatively to 1 liter of the above mixture under constant magnetic stirring. The mixture was stirred overnight in cold room. A clear solution was obtained. This solution is stored in a refrigerator at about 4° C. till used.

EXAMPLE IV

The starting materials for preparation of the solution were as follows:

| | |
|---|---|
| Sucrose | 76 g |
| Trisodium citrate, monohydrate | 7.35 g |
| Citric acid | 0.035 g |
| EDTA Na$_2$ | 0.050 g |
| Mannitol | 1.8 g |
| Propylmethylcellulose | 1.00 g |
| H$_2$O | 1 L |
| Retinol | 120 mg |
| Tween ®-80 | 500 mg |

The solution is prepared by adding sodium chloride, trisodium citrate, citric acid monohydrate, EDTA Na$_2$, mannitol and propylmethylcellulose in the amounts specified above to one liter of water. The foregoing constituents are dissolved and autoclaved at a pressure of 15 lbs. and a temperature of 120° C. and chilled to 4° C. 120 mg of retinol are dissolved in 500 mg of Tween ®-80 by gentle warming at about 50° C. and shaking by hand and transferred quantitatively to 1 liter of the above mixture under constant magnetic stirring. The mixture was stirred overnight at 4° C. A clear solution is obtained. This solution is stored in a refrigerator at about 4° C. till used.

EXAMPLE V

A 0.5 fluid oz. eye dropper bottle was filled with 15 ml. of a sterile aqueous solution containing:

| | per 1 ml |
|---|---|
| Retinol | 120 μg |
| Tween ®-80 | 0.5 mg |
| Nacl | 6.85 mg |
| Na$_3$ citrate, monohydrate | 7.35 mg |
| Citric acid | .031 mg |
| EDTA Na$_2$ | .05 mg. |
| Mannitol | 1.8 mg |
| Q.S. water | up to 1 ml |

Two drops of the solution were placed in one eye of an individual suffering from dry, irritated eyes two times a day, once in the morning and once in the evening, for a period of 30 days. An unpreserved normal saline solution was placed in the other eye using the same schedule for comparison purposes. The eye being treated showed a marked improvement in subjective comfort and appearance compared to the saline solution treated eye.

The use of the term "solution" in the aforementioned specification is not to be construed as meaning a true solution according to pure technical definition. It is rather to be construed as meaning a mixture which appears to the naked eye to be a solution, and accordingly, the word "solution" is to be construed as covering transparent emulsions of solubilized retinol, its derivatives and precursors.

The foregoing detailed specification has been given for the purpose of explaining and illustrating the invention. It is to be understood that the invention is not limited to detailed information set forth, and that various modifications can be made. It is intended to cover such modifications and changes as would occur to one skilled in the art, as the following claims permit and consistent with the state of the prior art.

I claim:

1. An ophthalmic preparation, which comprises:
   a. an aqueous solubilized Vitamin A composition selected from the group consisting of retinol, retinol derivatives, and admixtures thereof;
   b. a physiologically acceptable free radical scavenger;
   c. a physiologically compatible metal chelating agent for multivalent metal cations present in human and animal external eye tissue or tear film; and
   d. an agent inhibiting activity of polymorph nuclear leucocytes.

2. The ophthalmic preparation of claim 1 wherein the Vitamin A composition is retinol.

3. The opthalmic preparation of claim 1 wherein the metal chelating agent is ethylenediamine tetraacetate.

4. The ophthalmic preparation of claim 2 wherein the metal chelating agent is ethylenediamine tetraacetate.

5. The ophthalmic preparation of claim 1 wherein the metal chelating agent is a borate.

6. The opthalmic preparation of claim 2 wherein the metal chelating agent is a borate.

7. The opthalmic preparation of claim 1 wherein the free radical scavenger is mannitol.

8. The opthalmic preparation of claim 2 wherein the free radical scavenger is mannitol.

9. The ophthalmic preparation of claim 3 wherein the free radical scavenger is mannitol.

10. The opthalmic preparation of claim 4 wherein the free radical scavenger is mannitol.

11. The opthalmic preparation of claim 5 wherein the free radical scavenger is mannitol.

12. The opthalmic preparation of claim 6 wherein the free radical scavenger is mannitol.

13. The opthalmic preparation of claim 1 wherein the tonicity of the solution is adjusted within the range of 300±25 mOsm per kg of the solution by the addition of a compound selected from the group consisting of sodium chloride, potassium chloride, sucrose and mixtures thereof.

14. The opthalmic preparation of claim 2 wherein the tonicity of the solution is adjusted within the range of 300±25 mOsm per kg of the solution by the addition of a compound selected from the group consisting of sodium chloride, potassium chloride, sucrose and mixtures thereof.

15. The opthalmic preparation of claim 3 wherein the tonicity of the solution is adjusted within the range of 300±25 mOsm per kg of the solution by the addition of a compound selected from the group consisting of sodium chloride, potassium chloride, sucrose and mixtures thereof.

16. The opthalmic preparation of claim 4 wherein the tonicity of the solution is adjusted within the range of 300±25 mOsm per kg of the solution by the addition of a compound selected from the group consisting of sodium chloride, potassium chloride, sucrose and mixtures thereof.

17. The ophthalmic preparation of claim 5 wherein the tonicity of the solution is adjusted within the range of 300±25 mOsm per kg of the solution by the addition of a compound selected from the group consisting of sodium chloride, potassium chloride, sucrose and mixtures thereof.

18. The ophthalmic preparation of claim 6 wherein the tonicity of the solution is adjusted within the range of 300±25 mOsm per kg of the solution by the addition of a compound selected from the group consisting of sodium chloride, potassium chloride, sucrose and mixtures thereof.

19. The ophthalmic preparation of claim 7 wherein the tonicity of the solution is adjusted within the range of 300±25 mOsm per kg of the solution by the addition of a compound selected from the group consisting of sodium chloride, potassium chloride, sucrose and mixtures thereof.

20. The ophthalmic preparation of claim 8 wherein the tonicity of the solution is adjusted within the range of 300±25 mOsm per kg of the solution by the addition of a compound selected from the group consisting of sodium chloride, potassium chloride, sucrose and mixtures thereof.

21. The ophthalmic preparation of claim 9 wherein the tonicity of the solution is adjusted within the range of 300±25 mOsm per kg of the solution by the addition of a compound selected from the group consisting of sodium chloride, potassium chloride, sucrose and mixtures thereof.

22. The ophthalmic preparation of claim 10 wherein the tonicity of the solution is adjusted within the range of 300±25 mOsm per kg of the solution by the addition of a compound selected from the group consisting of sodium chloride, potassium chloride, sucrose and mixtures thereof.

23. The ophthalmic preparation of claim 11 wherein the tonicity of the solution is adjusted within the range of 300±25 mOsm per kg of the solution by the addition of a compound selected from the group consisting of sodium chloride, potassium chloride, sucrose and mixtures thereof.

24. The ophthalmic preparation of claim 12 wherein the tonicity of the solution is adjusted within the range of 300±25 mOsm per kg of the solution by the addition of a compound selected from the group consisting of sodium chloride, potassium chloride, sucrose and mixtures thereof.

25. The ophthalmic preparation of claim 13 wherein the tonicity of the solution is adjusted within the range of 300±25 mOsm per kg of the solution by the addition of a compound selected from the group consisting of sodium chloride, potassium chloride, sucrose and mixtures thereof.

26. The ophthalmic preparation of claim 1 wherein said inhibiting agent is comprised of citric acid and a citrate selected from the group consisting of sodium citrate, potassium citrate and combinations thereof.

27. The ophthalmic preparation of claim 2 wherein said inhibiting agent is comprised of citric acid and a citrate selected from the group consisting of sodium citrate, potassium citrate and combinations thereof.

28. The ophthalmic preparation of claim 3 wherein said inhibiting agent is comprised of citric acid and a citrate selected from the group consisting of sodium citrate, potassium citrate and combinations thereof.

29. The ophthalmic preparation of claim 4 wherein said inhibiting agent is comprised of citric acid and a citrate selected from the group consisting of sodium citrate, potassium citrate and combinations thereof.

30. The ophthalmic preparation of claim 7 wherein said inhibiting agent is comprised of citric acid and a citrate selected from the group consisting of sodium citrate, potassium citrate and combinations thereof.

31. The ophthalmic preparation of claim 8 wherein said inhibiting agent is comprised of citric acid and a citrate selected from the group consisting of sodium citrate, potassium citrate and combinations thereof.

32. The ophthalmic preparation of claim 9 wherein said inhibiting agent is comprised of citric acid and a citrate selected from the group consisting of sodium citrate, potassium citrate and combinations thereof.

33. The ophthalmic preparation of claim 12 wherein said inhibiting agent is comprised of citric acid and a citrate selected from the group consisting of sodium citrate, potassium citrate and combinations thereof.

34. The ophthalmic preparation of claim 13 wherein said inhibiting agent is comprised of citric acid and a citrate selected from the group consisting of sodium citrate, potassium citrate and combinations thereof.

35. The ophthalmic preparation of claim 14 wherein said inhibiting agent is comprised of citric acid and a citrate selected from the group consisting of sodium citrate, potassium citrate and combinations thereof.

36. The ophthalmic preparation of claim 15 wherein said inhibiting agent is comprised of citric acid and a citrate selected from the group consisting of sodium citrate, potassium citrate and combinations thereof.

37. The ophthalmic preparation of claim 18 wherein said inhibiting agent is comprised of citric acid and a citrate selected from the group consisting of sodium citrate, potassium citrate and combinations thereof.

38. The ophthalmic preparation of claim 19 wherein said inhibiting agent is comprised of citric acid and a citrate selected from the group consisting of sodium citrate, potassium citrate and combinations thereof.

39. The ophthalmic preparation of claim 20 wherein said inhibiting agent is comprised of citric acid and a citrate selected from the group consisting of sodium citrate, potassium citrate and combinations thereof.

40. The ophthalmic preparation of claim 21 wherein said inhibiting agent is comprised of citric acid and a citrate selected from the group consisting of sodium citrate, potassium citrate and combinations thereof.

41. The ophthalmic preparation of claim 22 wherein said inhibiting agent is comprised of citric acid and a citrate selected from the group consisting of sodium citrate, potassium citrate and combinations thereof.

42. The ophthalmic preparation of claim 23 wherein said inhibiting agent is comprised of citric acid and a citrate selected from the group consisting of sodium citrate, potassium citrate and combinations thereof.

43. The ophthalmic preparation of claim 24 wherein said inhibiting agent is comprised of citric acid and a citrate selected from the group consisting of sodium citrate, potassium citrate and combinations thereof.

44. An aqueous ophthalmic preparation of claim 26 wherein the pH is adjusted within a pH range of from about 6.6 to about 7.8.

45. The ophthalmic preparation of claim 44 wherein the pH of the solution is adjusted within a pH range of from about 7.1 to about 7.4 and the solution comprises from about 0.03 mg/ml. to about 0.06 mg/ml. of citric acid monohydrate and from about 5 mg/ml. of an alkali citrate to about 10 mg/ml. of trisodium citrate.

46. The ophthalmic preparation of claim 45 wherein retinol is present in an amount of from about 100 to about 1,000 I.U. per ml.

47. A retinol-containing aqueous ophthalmic preparation wherein pH is adjusted within a range of from about 6.6 to 7.8 by a buffering agent comprising a metabolic acid and a compound selected from the group consisting of sodium citrate, potassium citrate, sodium phosphates, potassium phosphates and combinations thereof.

48. The ophthalmic preparation of claim 47 wherein the sodium phosphates are selected from the group consisting of monosodium dihydrogenphosphate, disodium monohydrogenphosphate, dipotassium monohydrogenphosphate, monopotassium dihydrogenphosphate and mixtures thereof.

49. An ophthalmic preparation, which comprises:
(a) retinol present in aqueous solution in an amount up to about 1,000 I.U. per ml.;
(b) Tween®-80 present in an amount of from about 0.5 to about 1 mg/ml;
(c) NaCl or KCl present in an amount of from about 5 mg/ml. to about 10 mg/ml;
(d) citric acid present in an amount of from about 0.03 mg/ml. to about 0.06 mg.ml;
(e) sodium citrate or potassium citrate present in an amount of from about 5 mg/ml. to about 10 mg/ml.;
(f) ethylenediamine tetraacetate present in an amount of from about 0.05 mg/ml. to about 0.1 mg/ml.; and
(g) mannitol present in an amount of from about 0.9 to about 3.6 mg/ml.

50. The ophthalmic solution of claim 49 wherein the chloride component is NaCl, the citrate component is sodium citrate and the ethylenediamine tetraacetate is EDTA Na$_2$.

51. The ophthalmic preparation of claim 49 further comprising propylmethylcellulose present in an amount of from about 0.5 mg/ml. to about 1.5 mg/ml.

52. The ophthalmic preparation of claim 50 further comprising propylmethylcellulose present in an amount of from about 0.5 mg/ml. to about 1.5 mg/ml.

53. The method of treating dry eyes comprising the step of topically applying the ophthalmic preparation of claim 44 to the eye.

54. The method of treating dry eyes comprising the step of topically applying the ophthalmic preparation of claim 45 to the eye.

55. The method of treating dry eyes comprising the step of topically applying the ophthalmic preparation of claim 46 to the eye.

56. The method of treating dry eyes comprising the step of topically applying the ophthalmic preparation of claim 47 to the eye.

57. The method of treating dry eyes comprising the step of topically applying the ophthalmic preparation of claim 46 to the eye.

58. The method of treating dry eyes comprising the step of topically applying the ophthalmic preparation of claim 50 to the eye.

59. The method of treating dry eyes comprising the step of topically applying the ophthalmic preparation of claim 51 to the eye.

60. The method of treating dry eyes comprising the step of topically applying the ophthalmic preparation of claim 52 to the eye.

61. The method of treating dry eyes comprising the step of topically applying the ophthalmic preparation of claim 53 to the eye.

62. The method of treating dry eyes comprising the step of topically applying the ophthalmic preparation of claim 55 to the eye.

* * * * *